United States Patent [19]

Parkhurst et al.

[11] Patent Number: 4,954,659

[45] Date of Patent: Sep. 4, 1990

[54] 1,4-BIS (DIHYDROXYPHENYL) BUTANE AND ANALOGS

[75] Inventors: Robert M. Parkhurst, Redwood City; Ronald S. Pardini, Reno, both of Nev.

[73] Assignee: Chemex Pharmaceuticals, Inc., Denver, Colo.

[21] Appl. No.: 235,708

[22] Filed: Aug. 19, 1988

Related U.S. Application Data

[63] Continuation of Ser. No. 112,042, Oct. 21, 1987, abandoned, which is a continuation of Ser. No. 946,659, Dec. 24, 1986, abandoned, which is a continuation of Ser. No. 436,425, Oct. 25, 1982, abandoned.

[51] Int. Cl.$^5$ .................. C07C 43/164; C07C 39/12; C07C 33/26
[52] U.S. Cl. .................. 568/651; 568/637; 568/644; 568/646; 568/648; 568/650; 568/717; 568/721; 568/729; 568/808; 568/811
[58] Field of Search ............... 568/637, 644, 645, 729, 568/646, 650, 651, 648, 717, 721

[56] References Cited

U.S. PATENT DOCUMENTS 3,769,350 10/1973 Perry .............................. 568/644 X

OTHER PUBLICATIONS

Kharasch et al., "Grignard Reactions of Non-Metallic Substance", (1954), vol. 5, pp. 138–139.
Hilgetag et al., "Preparative Organic Chemistry", (1972), pp. 229, 232,361 and 369.
Biftu et al., "Jour. Chem. Soc. Perkins I", (1979), pp. 2276–2281.
Murphy et al., "Tetrahedron Letters", 22 (1981), p. 695–698.
Minato et al., "Tetrahedron Letters'", 21 (1980), p. 4017–4020.
Ward et al., "Tetrahedron Letters", 32 (1979), 3043–3046.
Fujii et al., Chem. Abs., vol. 83, (1975), 114,160 w.
Ronlan et al., Jour, Org. Chem., 39:7, (1974), 1014–1016.
Ayres et al., Tetrahedron, 25 (1969, 4093–4098.
Gisvold et al., Jour. Amer. Pharm. Assoc., 35 (1946), 188–191.

*Primary Examiner*—Werren B. Lone
*Attorney, Agent, or Firm*—Kenyon & Kenyon

[57] ABSTRACT

A grignard synthesis of pharmacologically active 1,4-bis(dihydroxyphenyl)butane and analogs, as well as novel intermediates, is provided, comprising preparing a grignard reagent preferably, a 3,4-dialkoxyphenyl propyl magnesium bromide, which may be reacted with carbonyl compounds to form intermediates of desired end products, said carbonyl compounds preferably being 3,4-dialkoxybenzaldehydes. The resulting alcohol is converted to a corresponding ether or siloxy compound, at the carbonyl site. The oxy-substituent is cleaved off; and the benzene ring or rings dealkylated to leave hydroxy substituents on the rings.

35 Claims, No Drawings

1,4-BIS (DIHYDROXYPHENYL) BUTANE AND ANALOGS

This application is a continuation of application Ser. No. 112,042 filed Oct. 21, 1987 now abandoned which is a continuation of application Ser. No. 946,659 filed Dec. 24, 1986 now abandoned, which is a continuation of application Ser. No. 436,425 filed Oct. 25, 1982 now abandoned.

TECHNICAL FIELD

This invention pertains to organic compounds and their syntheses, in particular, to a Grignard synthesis of 1,4-bis(dihydroxyphenyl)butane and pharmacologically active analogs.

BACKGROUND OF THE INVENTION 1,4-bis(dihydroxyphenyl)butane (desmethylnordihydroguaiaretic acid) is useful as an antioxidant, such as for food preservation purposes.

Nordihydroguaiaretic acid has been used as an antioxidant, but is expensive both to procure from natural sources such as the creosote bush *Larrea divaricata*, or *Larrea tridentata*, and to synthesize, requiring starting materials not readily available commercially, or a multiplicity of processing steps, such as those disclosed in U.S. Pat. Nos. 2,456,443; 2,644,822; 3,769,350; 3,843,728; and 3,906,004, as well as C. W. Perry, M. V. Kalnins and K. H. Deitcher, "Synthesis of Lignans, I. Nordihydroguaiaretic Acid," 37 J. Org. Chem., 4371 (1972).

In contrast to nordihydroguaiaretic acid, 1,4-bis(-dihydroxyphenyl)butane and its analogs may be easily and inexpensively synthesized using readily available reagents such as 3,4-methoxybenzaldehyde, or other substituted benzaldehydes. The substituted benzaldehyde is converted to a substituted phenylpropanol, which is halogenated and converted to a novel grignard reagent, such as 3,4-dimethoxyphenylpropyl magnesium bromide. This grignard reagent may be reacted with carbonyl compounds to produce intermediates for 1,4-bis-(3,4-dihyroxyphenyl)butane synthesis and a number of other novel compositions.

Prior Art Statement

O. Grisvold, D. Buelow and E. H. Carlson, *J. Am. Pharm. Assoc.* 35, 188-91 (1946) describes the preparation of 1,4-bis(3,4-dihydroxyphenyl)butane from veratraldehyde and succinic acid via 1,4-bis(3,4-dimethoxyphenyl), 1-3-butadiene and 1,4-bis(3,4-dimethoxyphenyl)butane, which is hydrogenated in glacial acetic acid and acetic anhydride with 48 percent hydrogen bromide, refluxing for two hours, to form a product melting at 141-142° C. The same article describes an alternate synthesis of the same compound via 1,4-bis(3,4-methylenedioxyphenyl)-1,3-butane prepared from the 1,3-butadiene obtained from a Kuhn synthesis with piperonal and succinic acid. Poor yields were reported.

A. Minato, K. Tameo, K. Suzuki, and M. Kumada, "Synthesis of a Lignan Skeleton via Nickel and Palladium-Phosphate Complex Catalyzed Grignard Coupling Reaction of Halothiophenes," Tetrahedron Lett. 21, 4017 (1980), describes the grignard reagents benzyl magnesium chloride, phenylmagnesium bromide, 4-methoxyphenyl magnesium bromide, 3,4-dimethoxyphenyl magnesium bromide, and 3,4-methylenedioxyphenylmagnesium bromide which are reacted with thiophenes, and the phenylthiopenes desulfurized to form lignans including 3,4-methoxy- and 3,4-methylenedioxy- ethers of nordihydroguaiaretic acid.

W. S. Murphy and S. Wattanasin, "Reductive Cleavage of Cyclopropyl Ketones," *Tetrahedron Lett.* 22, 695 (1981) describes the preparation of 1,4-bis(3,4-dimethoxyphenyl 1-butanone from 1-(3,4-dimethoxyphenyl), 2-(3,4-dimethoxybenzoyl) cyclopropane with zinc and zinc chloride, refluxing in ethanol for 30 hours.

A. Ronlan and V. D. Parker, "Electrosynthesis of Medium and Large-Sized Rings by Oxidative Cyclization of Bis(3,4-dimethoxyphenyl) Alkanes," *J. Org. Chem.* 39, 1014 (1974) depicts 1,4-bis(3,4-dimethoxyphenyl)butane as a starting material.

R. S. Ward, P. Satyanarayana, L. Ramachandra Rao, and B. V. Gopala Rao, "The Case for a Revised Structure for Hypophyllanthin - an Analysis of the C.N.M.R. Spectra of Aryltetralins," *Tetrahedron Lett.* 3043 (1979), depicts several racemic 2,3-dialkyl, 6,7-dialkoxy-1-(3,4-dimethoxyphenyl) tetralins. D. C. Ayres and R. B. Chater, "Lignans by Gas Chromatography,"*Tetrahedron Lett.* 25, 4093 (1969) discloses 2,3-dimethyl tetralins with various alkoxy substituents on the benzene rings.

Although several of the intermediates in the synthetic methods of this invention namely, 1,4-bis-(3,4-dimethoxyphenyl) have been depicted butane; 1,4-bis-(3,4-dihydroxyphenyl)-4-oxy-butane; in the above-described prior art, the novel grignard reagent, the methods themselves, and many resultant compositions have not been shown.

SUMMARY OF THE INVENTION

A grignard reagent is prepared from an aralkyl composition comprising a benzene ring having etheric substituents at positions 2, 3, 4, 5 and/or 6, preferably at positions 3 and 4, and an alkyl chain at position 1, preferably a 3-carbon chain, having a hydroxy group at the end carbon. The etheric substituents on the benzene ring remain unchanged during the grignard formation reaction and subsequent reactions of the grignard reagent with appropriate carbonyl-containing compositions, until the final step when the last intermediate is dealkylated to convert these etheric groups to hydroxyl groups.

Preferably a halogenated disubstituted phenylpropane is prepared from the corresponding alcohol, said halogenated composition having the form:

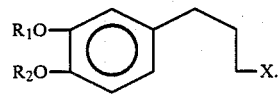

I where $R_1$ and $R_2$ are independently lower alkyl, alkenyl, aralkyl, or aralkenyl, or, taken together may form a lower alkylene radical; and
is chlorine, bromine or iodine.

A grignard reagent is then synthesized from the foregoing composition of the form:

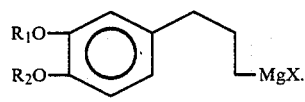

II

This grignard reagent is then reacted with a carbonyl-containing composition of the form:

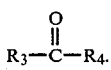  III where $R_3$ is H, alkyl, alkenyl, alkynyl, aryl, or a heterocyclic or polynuclear aromatic group, or combination containing two aryl, heterocyclic or polynuclear aromatic groups, or an aryl, heterocyclic, polynuclear aromatic group, or combination joined to the carbonyl by a lower alkyl, alkenyl or alkynyl chain, and the rings thereof may bear OH, $NH_2$, SH, $OCH_3$, COOH, or halogen substituents; and $R_4$ is $R_3$ or $OR_3$; to form compositions of the form:

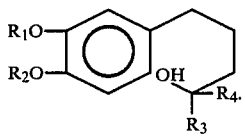  IV where $R_1$, $R_2$, $R_3$ and $R_4$ are as above. A corresponding ether is formed from the alcohol, of the form:

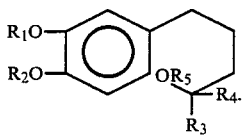  V where $R_5$ is a lower alkyl, alkenyl, aryl, aralkyl or aralkenyl, or silyl or substituted silyl with from one to three substituents which are, independently, lower alkyl, alkenyl, aryl, aralkyl or aralkenyl groups.

The etheric is group then cleaved from the 1-butane position under mild conditions which do not affect the etheric substituents on the benzene ring to form a compound of the form:

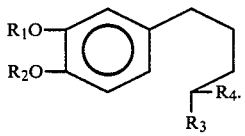  VI (it being understood that cleavage of $R_4$ will also occur when $R_4$ is an alkoxy, araloxy or aralkoxy group).

The compound is then dealkylated to convert the 3,4-substituents on the benzene ring to hydroxy groups, to form compounds of the form:

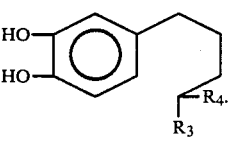  VII (it being understood that where $R_3$ and $R_4$ contain alkoxy phenyls, these will also be converted to hydroxyphenyls).

Where 1,4-bis(dihydroxyphenyl)butane is the desired end product, the grignard reagent is 1-magnesium bromo-3(3,4-dimethoxyphenyl)propane which is reacted with 3,4-dimethoxy-benzaldehyde, or other 3,4-substituted alkoxy benzaldehydes, to form 1,4-bis (3,4-alkoxyphenyl)1-butanol, which is converted to the ether at the 1-butane position, cleaved to remove the ether substituent from the 1-butane position, and finally dealkylated to form the desired product:

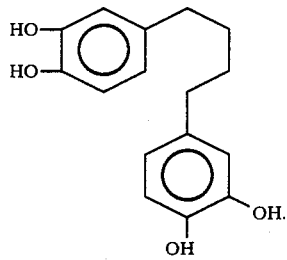  VIII

Additional compositions which may be prepared using the grignard reagent of this invention include those listed below. The specific carbonyl compound to be reacted with the 3,4-dimethoxyphenyl propyl magnesium bromide grignard reagent to produce each desired end product is also listed, these carbonyl compounds being commercially available, or readily prepared from commercially available compounds by means known to the art:

| Intermediate Carbonyl Compound | Desired End Product |
|---|---|
| 1. Benzahdehyde | 1-(3,4-dihydroxyphenyl),4-phenyl butane |
| 2. 3,4-5-trimethoxybenz-aldehyde | 1-(3,4-dihydroxyphenyl),4-(3,4,5-trihydroxyphenyl) butane |
| 3. 2,3,4-trimethoxybenz-aldehyde | 1-(3,4-dihydroxyphenyl),4-(2,3,4-trihydroxyphenyl) butane |
| 4. 2,5-dimethoxybenz-aldehyde | 1-(3,4-dihydroxyphenyl),4-(2,5-dihydroxyphenyl) butane |
| 5. 2,4-dimethoxybenz-aldehyde | 1-(3,4-dihydroxyphenyl),4-(2,4-dihydroxyphenyl) butane |
| 6. 3,5-dimethoxybenz-aldehyde | 1-(3,4-dihydroxyphenyl),4-(3,5-dihydroxyphenyl) butane |
| 7. 2,3-dimethoxybenz-aldehyde | 1-(3,4-dihydroxyphenyl),4-(2,3-dihydroxyphenyl) butane |
| 8. 3-hydroxy, 4-carboxyl-benzaldehyde | 1-(3,4-dihydroxyphenyl), 4(3-hydroxy,4-carboxyl-phenyl) butane |
| 9. 3,5-ditertbutyl, 4-hydroxy-benzaldehyde | 1-(3,4-dihydroxyphenyl), 4-(3,5-ditertbutyl,4-hydroxy-phenyl) butane |
| 10. 4-formyl-pyridine | 1-(3,4-dihydroxyphenyl), 4-pyridinyl-butane |
| 11. 3-pyridinecarbox-aldehyde | 1-(3,4-dihydroxyphenyl),4-(3-pyridinyl) butane |
| 12. 5-formyl-8-hydroxy-quinoline | 1-(3,5-dihydroxyphenyl), 4-[5-(8-hydroxy)quinoline] butane |
| 13. glucose tetramethyl-ether | 1-(3,4-dihydroxyphenyl), 4,6,7,8,9-pentahydroxy-nonane |
| 14. 2-formyl-thiophene | 1-(3,4-dihydroxyphenyl), 4-(2-thienyl) butane |
| 15. 3,4-disulfhydrylbenz-aldehyde | 1-(3,4-dihydroxyphenyl), 4(3,4-disulfhydryl) butane |
| 16. 4-alkanylbenzaldehyde | 1-(3,4-dihyroxyphenyl), 4-(4-alkanylphenyl) butane |
| 17. benzophenone | 1-(3,4-dihydroxyphenyl), |

-continued

| Intermediate Carbonyl Compound | Desired End Product |
|---|---|
| 18. polyacrolein | 4-diphenylbutane 1-[4-(3,4-dihydroxyphenyl-butanyl)] polyallyl alcohol |
| 19. terephthaldehyde | 1-4 bis[3,4-dihydroxy-phenyl)-butyl] benzene |
| 20. α,ω-alkandialdehyde | α,ω-bis[4-(3,4-dihydroxy-phenyl)-butanyl]-alkan-α,ω-diol |
| 21. alkanoic acid ester | 1,1-bis[4-(3,4-dihydroxy-phenyl)-butanyl] alkanol |
| 22. 2,5-thiophenedicarbox-aldehyde | 2,5-bis[3,5-dihydroxy-phenyl) butyl] thiophene |
| 23. 9-formyl anthracene | 1-(3,4-dihydroxyphenyl), 4-(9-anthryl)-butane |
| 24. 2,5-dimethoxyaceto-phenone | 2-(2,5-dihydroxyphenyl), 5-(3,4-dihydroxyphenyl) pentane |
| 25. 3,4-dimethoxyaceto-phenone | 1,4-bis(3,4-dihydroxy-phenyl) pentane |

In addition, closed ring products such as 1-(3,4-dihydroxyphenyl), 6,7-dihydroxytetralin may be prepared from the process intermediate 1,4-bis(3,4-dimethoxyphenyl), 1-butanol and its analogs having the phenolic substituents above described by treatment of the said intermediate with hydrogen and a platinum catalyst in acid. The said intermediate and its analogs may also be dehydrated with warm alumina to produce 1,4-bis(3,4-dihydroxyphenyl), 1-butene.

Analogs of many of the above-listed compounds may be prepared having hydroxy substituents at different positions on one of the benzene rings, or three or more hydroxy substituents on one of the benzene rings instead of two, by beginning with a grignard reagent having etheric substituents at different positions on the benzene rings, or three or more etheric substituents on the benzene ring instead of two, and reacting this grignard reagent with the appropriate carbonyl-containing compound to form the desired analog. Similarly, a grignard reagent having hydroxy substituents at different positions on the benzene ring or three etheric substituents on the benzene ring, e.g. 3,4,5-trimethoxyphenyl propyl magnesium bromide, might be reacted with the appropriate carbonyl-containing compound having a 3,4-dimethoxyphenyl group, e.g. 3,4-dimethoxybenzaldehyde, to form the above-listed compositions which have a 2,5- 2,4- 3,5-, etc. disubstituted, or a trisubstituted, phenyl group at one end, and a 3,4-disubstituted phenyl group at the other.

DETAILED DESCRIPTION OF THE PREFERRED EMBODIMENT

As used throughout this application, the terms "lower alkyl", and "lower alkenyl" and "lower alkynyl" refer to both straight and branched chain hydrocarbon groups containing from 1 to 6 carbon atoms, such as methyl, ethyl, propyl, etc., and the term "lower alkoxy" refers to the corresponding methoxy, ethoxy, etc. groups. The term "lower alkylene" includes both straight and branched chain hydrocarbon groups containing from 1 to 6 carbon atoms, such as methyl, ethyl, propyl, etc., and the term "lower alkoxy" refers to the corresponding methoxy, ethoxy, etc. groups. The term "lower alkenyl" includes both straight and branched chain alkenyl radicals containing from 2 to 6 carbon atoms such as methylene, ethylene, propylene, butylene, isobutylene, etc. The term "lower aralkyl" refers to aralkyl groups containing from 7 to 14 carbon atoms, such as phenyl lower alkyl, i.e., benzyl, phenylethyl, etc. The term "halogen" includes all four halogens, i.e., iodine, bromine, chlorine, and fluorine.

In the most preferred embodiments described below, $R_1$ and $R_2$ are methyl groups, X is bromine, $R_3$ is 3,4-dimethoxyphenyl; $R_4$ is H, and $R_4$ is methyl, to produce as the end product 1,4-bis(3,4-dihydroxyphenyl)butane, although it is understood that $R_1$, $R_2$, $R_4$ and $R_5$ may be varied as above described to produce the same composition, and that $R_3$ and $R_4$ may be varied to produce related compositions.

Substituted benzaldehydes of the formula:

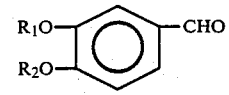

where $R_1$ and $R_2$ are independently lower alkyl, aralkyl, or, taken together may form a lower alkylene radical, preferably, 3,4-dimethoxybenzaldehyde, are converted to substituted cinnamic acids, preferably 3,4-dimethoxycinnamic acid. The benzaldehyde is preferably reacted with malonic acid in pyridine in the presence of piperdine. The reactants are mixed at a temperature of between about 25° C. and about 50° C., and the temperature is slowly raised over a period of about 1.5 hours to a reflux temperature of about 117° C. Refluxing is continued for between about 1.5 and about 2 hours, and the product precipitated with a strong acid, such as hydrochloric acid. A yield of between about 89.4 and about 100 percent is obtained by this method.

This cinnamic acid is then converted to the corresponding propionic acid, which is preferably 3,4-dimethoxyphenyl propionic acid, by hydrogenation, keeping the reaction clean of sulfur compounds. Preferably, the cinnamic acid is solubilized in a suitable solvent, such as ethanol, and subjected to between about 1 and about 20 pounds of hydrogen pressure at room temperature for a period of at least about 8 to 10 hours in the presence of a suitable catalyst, preferably rhodium on carbon. A yield of between about 90 and about 100 percent is obtained by this method.

Esterification of this propionic acid product is then conducted to form a corresponding ester, preferably 3,4-dimethoxyphenyl propionic acid methyl ester. Preferably esterification is performed by reacting the propionic acid, in suspension in a solvent such as methanol, and in the presence of 2,3-dimethoxypropane for the purpose of removing water during esterification, with an acetyl halide, preferably acetyl chloride. The reactants are allowed to remain in contact at room temperature for at least about ten hours, then refluxed for about an hour. Alternatively the materials may be allowed to remain in contact for about a week, and when this is done, refluxing is not necessary. A yield of between about 90 and about 100 percent is obtained by this method.

Reduction of the ester is then conducted to form the corresponding alcohol, preferably 3-(3,4-dimethoxyphenyl)-1-propanol. Preferably, the reduction is carried out using lithium aluminum hydride in a suitable solvent, such as tetrahydrofuran, under a nitrogen atmosphere. The starting materials must be kept dry. Gentle reflux conditions are maintained at about the boiling point of the tetrahydrofuran (65° C.), for a period of about 5 hours. The mixture is then cooled to a temperature of between about 20° C. and about 0° C., and a suitable reagent such as ammonium chloride is slowly added to form salts. After filtration, product is recovered from the filtrate by evaporation. To avoid contamination with impurities in the tetrahydrofuran hydrofuran solvent, additional product is extracted from the salts with methylene chloride. A total yield of up to about 100 percent is obtained by this method.

Halogenation of the alcohol is then performed, preferably by way of the corresponding sulfonate, preferably 3-(3,4-dimethoxyphenyl)1-propyl methanesulfonate. The preferred reaction for formation of this sulfonate is to react the alcohol under a nitrogen atmosphere with an appropriate sulfonyl chloride, preferably methanesulfonyl chloride, in the presence of a suitable base such as triethylamine. The reaction is carried out at a temperature of between about 0° C. and about −10° C., the reactants remaining in contact for between about 1 and 1.5 hours. A yield of up to 100 percent is obtained by this method.

The sulfonate is then converted to the corresponding halogenated composition, preferably 1-bromo,3-(3, 4-dimethoxyphenyl)propane. Preferably, the sulfonate is reacted with a suitable halogen salt, such as potassium bromide in the presence of acetonitrile and an 18-crown-6 which is soluble in the acetonitrile, such as dicyclohexano-18-crown-6, to coordinate potassium and make bromine ions available for the reaction. The reaction materials are refluxed for between about 22 and about 24 hours at about the boiling point of the acetonitrile (81° C.). Purification, such as by means of silica gel, may be necessary when impurities such as BHT are present. Otherwise, purification by vacuum distillation will suffice. A yield of between about 83 and about 100 percent is obtained by this method.

An alternate procedure for halogenation of the alcohol is direct halogenation by means of a phosphorus trihalide, preferable phosphorus tribromide, in a suitable solvent such as dry benzene or ether, in the presence of pyridine. The reaction is carried out under a nitrogen atmosphere at a temperature below about 0° C. Gradual warming over a period of between about 8 and about 12 hours to room temperature, followed by further warming to about 60° C. and solubilization in chloroform followed by evaporation gives a yield of between about 79 and about 100 percent.

A grignard reagent is then prepared from the halogenated compound. Preferably this grignard reagent is 1-magnesium-bromo,3-(3,4-dimethoxyphenyl)propane.

The halogenated composition may contain sufficient impurities to prevent grignard formation in the form of hydroxy-substituted compositions, such as 1-bromo,3-(3-methoxy4-hydroxyphenyl)propane, or a similar composition in which the hydroxy-substitution occurs in the 3-position rather than the 4-position. In this case additional purification methods may be necessary, such as gravity open silica gel column filtration using hexane-five percent acetone as a solvent.

Preferably the grignard formation reaction is conducted under a nitrogen atmosphere. Water and other hydroxylic compounds must be carefully eliminated. The halogenated composition is added dropwise to magnesium powder covered by a suitable solvent such as tetrahydrofuran, diethyl ether, or other solvents known to the art, to which a trace of a suitable halogen, such as iodine, has been added. A gentle reflux is maintained for a period of between about 2 and about 5 hours at an appropriate temperature for the solvent used. If tetrahydrofuran is used, the refluxing is conducted at a temperature of between about 25° C. and about 65° C. The mixture may then be stirred and refluxing continued for about 45 minutes longer.

The process of this invention does not require that the grignard reagent be isolated before being reacted with the desired carbonyl compounds as hereinafter described, nor that any of the subsequent intermediates up to the final intermediate be isolated. The final intermediate, i.e., the intermediate having the same structure as the final product except for the presence of etheric substituents on the benzene ring rather than the hydroxy substituents of the final product, is easily isolated and purified; and thus, a pure final product is obtained.

The grignard reagent above described may be reacted with carbonyl compounds to form a number of novel compositions. When the desired end product is 1,4-bis(dihydroxyphenyl)butane, or compounds analogous or homologous thereto, the grignard reagent is 1-magnesium bromo, 3-(3,4-dimethoxyphenyl)propane, and the carbonyl compound is preferably a substituted benzaldehyde.

When a substituted benzaldehyde, preferably 3,4-dimethoxybenzaldehyde, is reacted with the grignard reagent, an alcohol is produced by the well-known grignard synthesis reaction. Preferably, the alcohol formed is 1,4-bis(3,4-dimethoxyphenyl)butane-1-ol. Preferably the grignard reagent is cooled to about 0° C. and 3,4-dimethoxybenzaldehyde in a suitable solvent such as tetrahydrofuran is added over a period of about one hour at a temperature of between about 0° C. and about 3° C. The starting materials should be of high purity; and the reaction should be carried out in a dry, inert atmosphere. The mixture is allowed to warm to room temperature and stirred for a period of between about 8 and about 12 hours. The mixture is then cooled to about 0° C. and treated with saturated ammonium chloride solution at about this temperature. After several more hours at room temperature, product is obtained by filtration and evaporation of the filtrate. Additional product is extracted from the solids with methylene chloride. Some 1,4-bis(3,4-dimethoxyphenyl) 1-butanone may be formed along with the expected alcohol, and this may be converted to the alcohol with a suitable reducing agent such as sodium borohydride. An additional impurity, wherein one of the phenolic methoxy groups has been converted to a hydroxy, may also be present, but where the final product calls for replacement of all phenolic alkoxy groups with hydroxy groups, this impurity may be carried along through ensuing steps and will be converted to the desired end product. Based on these considerations, a maximum yield for the grignard synthesis reaction is obtained by this method.

From the alcohol produced by the foregoing grignard synthesis, a corresponding ether is prepared, preferably 1,4-bis(3,4-dimethoxyphenyl),1-methoxybutane. Preferably a suitable metal hydride, such as sodium hydride is added to the alcohol along with an alkyl halide, such as methyl iodine in solution in a suitable solvent such as tetrahydrofuran, dry dimethyl formamide or dimethyl sulfoxide. The reactants must be kept free of water and other hydroxylic solvents, and excess reagents over starting materials should be used. The reactants remain in contact at about room temperature for between about 0.5 and about 1 hour, then a small amount of water is stirred into the mixture, with stirring being continued for about one hour, followed by filtration and evaporation of the filtrate. Further purification, such as methylene chloride extraction may be conducted as necessary. Yields of between about 96 and about 100 percent are obtained using this method.

Cleavage of the ether at the 1-butane position is then conducted to leave a product in which all substituents have been removed from the site of the oxygen substituent on the original carbonyl compound reacted with the grignard reagent. Preferably, the compound formed by cleavage of the ether is 1,4-bis(3,4--dimethoxyphenyl) butane. A suitable reaction involves contacting anhydrous liquid ammonia which has been condensed with sodium under a nitrogen atmosphere, at dry ice temperature, and into which an alkali metal such as sodium has been stirred, with a solution of the ether in a suitable solvent such as tetrahydrofuran, which is added in several stages in order to maintain excess sodium. A blue color indicates the desired presence of excess sodium. Other reagents known to the art may be used to effect the cleavage, including lithium or potassium in lower alkyl amines; and other suitable solvents include ethyl ether and benzene. The mixture is allowed to react for at least about 20 minutes, but less than about an hour, carefully maintaining the temperature, followed by the addition of a solvent such as methanol and water, at which point the blue color disappears. The ammonia is evaporated off, and the residue treated with ice water. Recrystallization may be performed for further purification, a purity of more than 98.5 percent being obtainable by this method. A yield of between about 70 and about 100 percent is obtainable. If the time and temperature are not limited as above described, the substituents on the benzene rings, and the rings themselves, may be affected.

The product of the foregoing cleavage reaction is then dealkylated to convert the phenolic ether substituents to hydroxy groups. Preferably, the product formed from the 1,4-bis(3,4-dimethoxyphenyl)butane obtained by the preceding reaction is 1,4-bis(3,4-dihydroxyphenyl)butane. Preferably, a strong mineral halide acid, more preferably about a 48% solution plus or minus about 10%, of hydrogen bromide refluxed under a nitrogen atmosphere or contacted with a reducing agent such as sodium dithionate or thiosulfate to remove excess bromine, is contacted with the ether-substituted compound at about room temperature, and refluxing is continued for between about 8 and about 10 hours. Purification, such as by filtration through a material such as Celite (a trade name for diatomaceous silica, manufactured by Johns-Manville Company of Lompoc, Calif., in a suitable solvent such as diethyl ether and hexane, or treatment of the product material in solution in a suitable alcohol such as methanol with water and a reducing agent such as sodium dithionite, may be performed as required. The filtrate of crude, approximately 48% hydrobromic acid can be recycled for dealkylation of additional starting material. A yield of about 83 percent, of greater than 99 percent purity, may be obtained by this method. Critical to obtaining this yield is the use of excess acid and the complete exclusion of oxygen.

The invention is further illustrated by the following examples:

EXAMPLES

EXAMPLE 1

Preparation of Methyl 3-(3,4-dimethoxyphenyl)propionate

Acetyl chloride (20 cc) was added dropwise over 10 minutes with stirring to methanol (400 cc); the resulting solution was added all at once to a magnetically stirred suspension of 3-(3,4-dimethoxyphenyl)propionic acid (500 g, 2.378 moles) in methanol (1.6 l) and 2,3-dimethoxypropane (250 cc). The reaction mixture was stirred overnight at room temperature and then at reflux for 1 hour. After cooling, the solution was evaporated in vacuo to a light yellow syrup; yield: 533 g (100%).

EXAMPLE 2

Preparation of 3-(3,4-Dimethoxyphenyl)-1-propanol

To a 5 l, 3-neck flask, fitted with a condenser, mechanical stirrer and septum inlet, was added by needle/$N_2$ pressure a solution of lithium aluminum hydride in THF (1M, 912 cc). Methyl 3-(3,4-dimethoxyphenyl)-propionate (213 g, 0.95 mole) was dissolved in dry THF (total volume 900 cc and the resulting solution was added dropwise over a period of 5 hours using needle/$N_2$ pressure to the stirred LAH solution at a rate to maintain gentle reflux under a continuous $N_2$ atmosphere. The reaction mixture was stirred overnight at room temperature, cooled in an ice/acetone bath and treated dropwise over about 2 hours with saturated $NH_4Cl$ solution (104 cc), the nitrogen pressure being continued to this point. After stirring for several hours, the mixture was filtered and the salts were washed with dry THF. The filtrate was evaporated in vacuo to a light yellow oil; yield: 160 g. The salts from the above filtration were air-dried for several days, combined with $CH_2Cl_2$ (700 cc), stirred overnight and filtered. The filtrate was evaporated in vacuo to give an additional 26 g of product. The overall yield of a light yellow oil was: 186 g (100%).

EXAMPLE 3

Preparation of 3-(3,4-Dimethoxyphenyl)-1-propyl methanesulfonate

Under $N_2$, methanesulfonyl chloride (129.7 g, 1.132 m, 87.6 cc) was added dropwise over 1–1.5 hours at $-10°$ to 0° C. to a mechanically stirred solution of 3-(3,4-dimethoxyphenyl)-1-propanol (202 g, 1.03 mole) and $Et_3N$ (158.3 g, 1.56 mole, 218 cc) in $CH_2Cl_2$ (1.5 l) contained in a 5 l, 3-neck flask. The reaction mixture was stirred at 0° C. for 1 hour and then washed successively with icewater (1×700 cc), cold 3N HCl (1×700 cc), saturated $NaHCO_3$ solution (1×700 cc) and brine (1×700 cc). The organic solution was dried ($Na_2SO_4$) and concentrated in vacuo to an orange syrup; yield: 282 g (100%).

EXAMPLE 4

Preparation of 1-Bromo-3-(3,4-dimethoxyphenylpropane

In a 5 l, 3-neck flask, fitted with a mechanical stirrer and condenser were placed 3-(3,4-dimethoxyphenyl)-propyl methanesulfonate (282 g, 1.029 mole), KBr (282 g, 2.37 mole), dicyclohexano-18-crown-6 (19.2 g, 0.0515 mole) and dried MeCN (2.8 l). The mixture was stirred and refluxed for 22 hours, cooled, and filtered. The filtrate was evaporated in vacuo to an oil. The oil was dissolved in $CH_2Cl_2$ (1.5 l), washed with $H_2O$ (1×750 cc) and dried ($Na_2SO_4$). The solution was evaporated in vacuo to an orange oil; yield: 267 g.

The crude product (267 g) was applied neat to 1.3 Kg silica gel (90-200 mesh) which had been equilibriated with 1:1 $CH_2Cl_2$:hexane and was contained in a 10 cm O.D.×30 cm column. Elution with 1:1 $CH_2Cl_2$:hexane gave a forerun (800 cc) and 5 fractions (200 cc each) which contained the desired product and an impurity. Evaporation in vacuo of the 5 fractions gave 140 g of impure desired product.

Further elution with 2:1 $CH_2Cl_2$:hexane gave 23 fractions (200 cc each) which contained desired product only. Evaporation in vacuo of these fractions gave 120 g of pure desired product.

The impure material from above (140 g) was applied neat to 1.3 Kg silica gel (90-200 mesh) which had been equilibriated with hexane and was contained in a 10 cm O.D.×30 cm column. Elution with hexane (2 l) followed by 10:1 hexane: $CH_2Cl_2$(5 l) removed the impurity. Elution with $CH_2Cl_2$ (6.5 l) removed the desired product. Evaporation in vacuo gave 102 g of pure desired product. The combined yield of desired product, a pale yellow oil, was: 222g (83%).

EXAMPLE 5

Preparation of 1,4-bis(3,4-Dimethoxyphenyl)butane-1-ol

Under $N_2$, Mg powder (21.15 g, 0.87 gram-atom) was added to a 5 l, 3-neck flask fitted with a mechanical stirrer, condenser, and septum inlet. The Mg was covered with dry THF (200 cc), stirring was begun and a trace of iodine was added followed by about 20 cc then dropwise addition of a solution of 1-bromo,3-(3,4-dimethoxyphenyl)propane (222 g, 0.857 mole) from which all traces of water had been removed in dry THF (1150 cc) at a rate to maintain gentle reflux over a period of 2.5 hours. The resulting dark grey solution was stirred and refluxed for 45 minutes and then cooled to 0° C. With stirring a solution of dried 3,4-dimethoxybenzaldehyde (149.5 g, 0.899 mole) in dry THF (150 cc) was added dropwise over 1 hour at 0° C.-3° C. The resulting mixture was stirred overnight at room temperature, cooled to 0° C., and treated over ½ hour at 0°-5° C. with saturated $NH_4Cl$ solution (100 cc). The nitrogen atmosphere was discontinued at this point. After standing at room temperature for several hours, the mixture was filtered and the solids were air-dried overnight. The filtrate was evaporated in vacuo to a syrup. The solids were extracted with $CH_2Cl_2$ (500 cc) by stirring for a few hours and filtering. The filtrate was combined with the syrup from above and the mixture was diluted with $CH_2Cl_2$ (1:1) The organic solution was washed with $H_2O$ (3 ×500 cc), dried (Na ), and evaporated in vacuo to a light orange syrup; yield: 300 g (>100%).

Preparation of 1,4-bis(3,4-Dimethoxyphenyl-1-methoxybutane

A 60% dispersion of NaH in mineral oil (32.7 g, 1.3625 mole) was added portionwise over 40 minutes to a mechanically stirred solution of 1,4-bis (3,4-dimethoxyphenyl)butane-1-ol (292 g, 0.843 mole), MeI (125.4 g, 0.883 mole, 55 cc), and dry THF (1.5 l) at 22°-33° C. maintained by intermittent cooling. Additional MeI (22.8 g, 0.16 mole, 10 cc) was added and the reaction mixture was stirred overnight at room temperature. The reaction mixture was treated with $H_2O$ (15 cc), stirred for 1 hour, and filtered. The filtrate was evaporated in vacuo to a syrup; the syrup was treated with $CH_2Cl_2$ (1 l) and $H_2O$ (500 cc) and the phases were separated. The aqueous phase was extracted with $CH_2Cl_2$ (1×500 cc). The combined organic phase was washed with $H_2O$ (3×400 cc), dried (Na ) and evaporated in vacuo to a yellow syrup; yield: 293 g (96%).

EXAMPLE 7

Preparation of 1,4-Bis(3,4-dimethoxyphenyl)butane

Ammonia (1.6 l) was condensed into an oven-dried 2 l three-neck flask containing a few pieces of sodium under nitrogen. The ammonia (1.2 l) was recondensed into another oven-dried 3 l three-neck flask at dry ice temperature. Ten grams of sodium cut into small pieces was added to the stirring ammonia and stirring continued for 15 minutes and then a solution of 1,4-bis (3,4-dimethoxyphenyl)-1-methoxybutane (98.5 g) in 200 ml of dry THF which had been cooled in dry ice was added as rapidly as possible using a needle transfer under nitrogen pressure. The blue color faded toward the end of the addition and 6 g more sodium was added to reestablish the blue color. The remaining starting product in THF was added followed by another 100 ml of dry THF to wash the addition apparatus. After a total of 15 minutes reaction time from start of the addition of the starting product, 100 ml of methanol was added, followed by 75 ml methanol:water (1:1). The presence of starting material in the product indicates reaction time should be extended to 20-25 min.; however reaction times in excess of an hour give Birch reduction products.

The ammonia was allowed to evaporate overnight, the residue evaporated in a vacuum and treated with 1.5 l of ice water. The solid was collected by filtration, washed with water and air dried, and gave 85 g of crude product. The crude product was recrystallized from 450 ml methanol:water (10:3) to give 63.8 g (70.7% theor.) colorless plates of 98.6% purity.

EXAMPLE 8

Preparation of 1,4-Bis(3,4-dihydroxyphenyl)butane

Four pints of 48% HBr (1.89 l) was placed in a 3 l three-neck flask with reflux condenser, thermometer, and nitrogen inlet. The outlet was from the top of the condenser to a conc. sulfuric acid bubble trap. The mag. stirred glasscol heated flask and HBr was refluxed under nitrogen. Twenty-five ml of HBr was distilled off to remove some bromine. The flask was allowed to cool to room temperature under nitrogen and 40 g of 1,4-bis(3,4-dimethoxyphenyl)butane added. The mixture turned wine red and was refluxed under nitrogen for 9 hours. At the end of this time stirring was continued and the mixture allowed to cool slowly overnight to give a slurry of fine grey crystals in the red solution. After cooling to ice temperature the solids were collected on a glass filter and washed with ice water, and air dried to give 27.6 g (83.3% theor.) of crude product.

The crude product (43.75 g) was dissolved in 400 ml of diethyl ether and hexane added until cloudy (approx. 200 ml). A small amount of ether removed the cloud again and the solution was filtered through a thin layer of Celite to remove a very small amount of black gum. The ether-hexane was evaporated in a vacuum and the residue dissolved in 400 ml of methanol. Four liters of hot water was added slowly to the methanol solution.

The solution was kept warm while a trace of sodium dithionite was added to destroy the brown color. Upon cooling slowly and seeding and finally cooling to ice temperature the product was collected as almost colorless crystals 43 g, mp 142° C., purity 99.66 percent by gas chromatography. Analysis for carbon gave 70.06% and for hydrogen gave 6.57 percent. Calculated for $C_{16}H_{18}O_4$ is carbon 70.05%, hydrogen 6.61%.

Although the foregoing invention has been described in some detail by way of illustration and example for purposes of clarity of understanding, it will be obvious that certain changes and modifications may be practiced within the scope of the invention, as limited only by the scope of the appended claims.

We claim:

1. A compound selected from the group consisting of compounds of the formula:

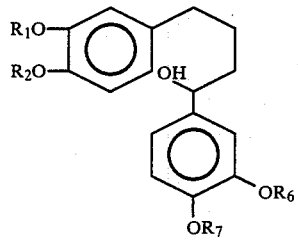

where $R_1$ and $R_2$ and $R_6$ and $R_7$ may be lower alkyl, C2–C6 alkenyl, an aromatic substituent containing up to three carbon containing aromatic rings and may contain sulfur or nitrogen, C7–C14 aralkyl or C7–C14 aralkenyl, or $R_1$ and $R_2$ and $R_6$ and $R_7$ taken together form a lower alkylene radical, or $R_6$ and $R_7$ are H.

2. The compound of claim 1 wherein $R_1$, $R_2$, $R_6$ and $R_7$ are methyl.

3. A compound selected from the group consisting of compounds of the formula:

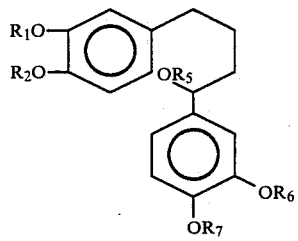

where $R_1$ and $R_2$, and $R_6$ and $R_7$ may be lower alkyl, C2–C6 alkenyl, an aromatic substituent containing up to three carbon containing aromatic rings and may contain sulfur or nitrogen, C7–C14 aralkyl or C7–C14 aralkenyl, or $R_1$ and $R_2$, and $R_6$ and $R_7$ taken together form a lower alkylene radical, or $R_6$ and $R_7$ are H; and $R_5$ is a lower alkyl, C2–C6 alkenyl, an aromatic substituent containing up to three carbon containing aromatic rings and may contain sulfur and/or nitrogen, C7–C14 aralkyl or C8–C14 aralkenyl, or silyl, or substituted silyl with from one to three substituents which may be lower alkyl, C2–C6 alkenyl, an aromatic substituent containing up to three carbon containing aromatic rings and may contain sulfur or nitrogen, C7–C14 aralkyl or C8–C14 aralkenyl groups.

4. The compound of claim 3 wherein $R_1$, $R_2$, $R_5$, $R_6$ and $R_7$ are methyl.

5. A composition of matter consisting of 1-(3,4-dihydroxyphenyl), 4-(3,4,5-trihydroxyphenyl)butane.

6. A composition of matter consisting of 1-(3,4-dihydroxyphenyl), 4-(2,3,4-trihydroxyphenyl)butane.

7. A composition of matter consisting of 1-(3,4-dihydroxyphenyl), 4-phenyl butane.

8. A composition of matter consisting of 1-(3,4-dihydroxyphenyl), 4-(3,5-ditertbutyl, 4-hydroxyphenyl)butane.

9. A composition of matter consisting of 1-(3,4-dihydroxyphenyl), 4-(2,5-dihydroxyphenyl)butane.

10. A composition of matter consisting of 1-(3,4-dihydroxyphenyl), 4-(2,4-dihydroxyphenyl)butane.

11. A composition of matter consisting of 1-(3,4-dihydroxyphenyl), 4-(3,5-dihydroxyphenyl)butane.

12. A composition of matter consisting of 1-(3,4-dihydroxyphenyl), 4(2,3-dihydroxyphenyl)butane.

13. A compound of the formula:

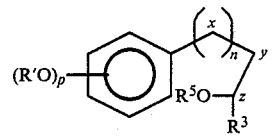

wherein p may be 1 to 4;

$R^1$ may independently be H, C1–C6 alkyl, C2–C6 alkenyl, an aromatic substituent containing up to three carbon containing aromatic rings and may contain sulfur and nitrogen, C7–C14 aralkyl, and when attracted to two adjacent ($R^1O$) groups may be lower alkylene;

$R^3$ may be an aromatic substituent containing up to three carbon containing rings and which may contain nitrogen or sulfur optionally substituted by up to three substituents selected from the group consisting of hydroxy, halogen, amino, carboxy, alkoxy or lower alkyl; said $R_3$ may be joined to the z carbon directly, or by a C1–C6 alkyl or a C2–C6 alkenyl chain which may be interrupted by a phenylene group;

$R^5$ may be H, C1–C6 alkyl, C2–C6 alkenyl, an aromatic substituent containing up to three carbon containing aromatic rings which may also contain sulfur or nitrogen, or C7–C14 aralkyl;

n may be 0 to 4; and

Carbons x, y and z may be substituted with hydrogen or one or more lower alkyl groups, said lower alkyl groups may be joined in a ring.

14. A composition of matter consisting of 1,4-Bis(1,4-Bis(3',4'-dimethoxyphenyl)-1-methoxybutane.

15. A composition of matter consisting of 1,4-Bis(1,4-Bis(3',4'-dihydroxyphenyl)-1-methoxybutane.

16. A composition of matter consisting of 1,4-Bis(1,4-Bis(3',4'-dimethoxyphenyl)-1-hydroxybutane.

17. A composition of matter consisting of 1,4-Bis(1,4-Bis(3',4'-dihydroxyphenyl)-1-hydroxybutane.

18. A composition of matter consisting of 1,4-Bis(1,4-Bis(3',4'-dihydroxyphenyl)-2-methoxybutane.

19. A composition of matter consisting of 1,4-Bis(3',4'-dihydroxyphenyl)-2,3-dimethoxybutane.

20. A compound of the formula

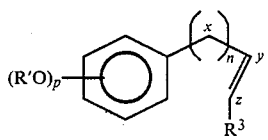

wherein
   p may be 2 to 4
   $R^1$ may independently be H, C1–C6 alkyl, C2–C6 alkenyl, an aromatic substituent containing up to three carbon containing aromatic rings which may also contain sulfur or nitrogen, C7–C14 aralkyl, and when attached to two adjacent ($R^1O$) groups may be lower alkylene;
   $R^3$ may be an aromatic substituent containing up to three carbon containing aromatic rings and which may contain nitrogen or sulfur optionally substituted by up to three substituents selected from the group consisting of hydroxy, halogen, amino, carboxy, alkoxy or lower alkyl; said $R^3$ may be joined to the z carbon directly or by a C1–C6 alkyl or a C2–C6 alkenyl chain which may be interrupted by a phenylene group;
   n may be 0 to 4; when n is 0, $(R^1O)_p$ shall be 2,3-, 2,4-, or 3,4-dihydroxy and $R_3$ shall be 2,3-, 2,4-, or 3,4dihydroxyphenyl, or their alkyl or aralkyl ethers, and carbons y and z may be substituted with lower alkyl groups; and
   Carbons x, y and z may be independently substituted with lower alkyl groups, said alkyl groups may be joined into a ring.
21. A composition of matter consisting of 1,4-Bis(3',4'-dihydroxyphenyl)-2,3-dimethylbutene-1.
22. A composition of matter consisting of 1,4-Bis(3',4'-dihydroxyphenyl)-2,3-dimethylbutene-2.
23. A composition of matter consisting of 1,4-Bis(3',4'-dihydroxyphenyl)-2,3-dimethylbutene-1,3.
24. A composition of matter consisting of 4-(3',4'-dihydroxyphenyl-1-(2-benzyloxy-5-hydroxyphenyl)-butene-1.
25. A composition of matter consisting of 1,3-Bis(3',4'-dihydroxyphenyl)-propane.
26. A composition of matter consisting of 1-(3',4'-dihydroxyphenyl)-3-(4'-hydroxyphenyl)-propene.
27. A composition of matter consisting of 1,2-Bis(3',4'-dihyroxyphenyl)-ethylene.
28. A compound of the formula

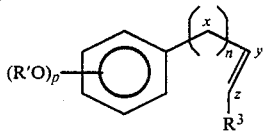

wherein
   p may be 2–4;
   $R^1$ is H, C1–C6 alkyl or C2–C6 alkylene;
   $R^3$ is phenyl independently substituted by up to 3 substituents selected from the group consisting of hydroxy, halogen, lower alkyl or lower alkoxy; and
   Carbons x, y and z may be substituted with lower alkyl groups; and
   n is 2.
29. The compound according to claim 28 whenever $R^1$ is H.

30. A compound of the formula

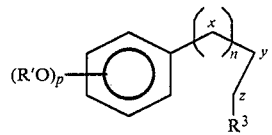

wherein
   p may be 2 to 4;
   $R^1$ may independently be H, C1–C6 alkyl, C2–C6 alkenyl, an aromatic substituent containing up to three carbon containing aromatic rings which may also contain nitrogen or sulfur, C7–C14 aralkyl, and when attached to two adjacent $R^1O$ groups may be lower alkylene;
   $R^3$ may be an aromatic substituent containing up to three carbon containing rings and which may contain nitrogen or sulfur optionally substituted by up to three substituents selected from the group consisting of hydroxy, halogen, amino, carboxy, alkoxy or lower alkyl and; said $R^3$ may be joined to the z carbon directly, or by a C1–C6 alkyl or a C2–C6 alkenyl chain which may be interrupted by a phenylene group;
   n may be 0 to 4;
   Carbons x, y and z may be substituted with lower alkyl groups and said lower alkyl groups may be joined into a ring; and
   $R^3$ may not be 3,4-dihydroxyphenyl when $(R^1O)_p$ is 3,4-dihydroxy, nor be 3,4-dimethoxyphenyl when $(R^1O)_p$ is 3,4dimethoxy, nor be 3,4-methylenedioxyphenyl when $(R^1O)_p$ is 3,4methylenedioxy and n is 1, or $R^3$ may not be 3,4-dihydroxyphenyl when $(R^1O)_p$ is 3,4-dihydroxy, nor be 3,4-dimethoxyphenyl when $(R^1O)_p$ is 3,4-dimethoxy, nor be 3,4-methylenedioxyphenyl when $(R^1O)_p$ is 3,4 methylenedioxy and n is 2 and carbon y and an x carbon contain only H or one methyl group on each carbon.
31. The compound according to claim 30 wherein n is 0, $(R',O)$ is 3,4-dihydroxy, and $R_3$ is 2-benzyloxy5-hydroxyphenyl.
32. A composition of matter consisting of 1-(3',4'-dihydroxyphenyl)-3-(4,-pyridyl)-2-methylpropane.
33. A composition of matter consisting of 1-(2',4'-dihydroxyphenyl)-4-(3,-hydroxy-4,-carboxyphenyl)-butane.
34. A composition of matter consisting of 1,2-Bis(3',4'-dihydroxyphenylmethyl)-cyclopentane.
35. A compound of the formula

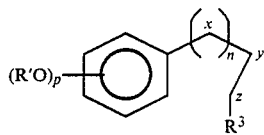

wherein
   p may be 2–4;
   $R^1$ is H
   $R^3$ is phenyl independently substituted by up to three substituents selected from the group consisting of hydroxy, halogen, lower alkyl, or alkoxy;
   Carbons x, y and z may be substituted with lower alkyl groups; and
   n may be 1 to 3.

* * * * *

UNITED STATES PATENT AND TRADEMARK OFFICE
CERTIFICATE OF CORRECTION

PATENT NO. : 4,954,659

DATED : September 4, 1990

INVENTOR(S) : Robert M. Parkhurst et al.

It is certified that error appears in the above-identified patent and that said Letters Patent is hereby corrected as shown below:

Column 1, line 43, "dihyroxyphenyl" should read
-- dihydroxyphenyl --.

Column 2, line 2, "phenylthiopenes" should read
-- phenylthiophenes --.

Column 2, line 28, "have been depicted" should be deleted.

Column 2, line 29, before "in" should be -- 1,4-bis-(3,4-dimethoxyphenyl)-4-oxy-butane; 1,4-bis-(3,4-methylenedioxyphenyl)-4-oxy-butane, --.

Column 2, line 59, before "is" should be -- X --.

Column 4, line 32, "Benzahdehyde" should read
-- Benzaldehyde --.

Column 4, line 66, "dihyroxyphenyl" should read
-- dihydroxyphenyl --.

Column 5, line 51, "EMBODIMENT" should read
-- EMBODIMENTS --.

Column 6, line 6, "$R_4$" should read -- $R_5$ --.

Column 7, line 38, "preferable" should read
-- preferably --.

Column 11, line 54, "(Na)" should read -- $(Na_2SO_4)$ --.

UNITED STATES PATENT AND TRADEMARK OFFICE
CERTIFICATE OF CORRECTION

PATENT NO. : 4,954,659

DATED : September 4, 1990

INVENTOR(S) : Robert M. Parkhurst et al.

It is certified that error appears in the above-identified patent and that said Letters Patent is hereby corrected as shown below:

Column 11, line 57, should read -- EXAMPLE 6 --.

Column 12, line 6, "(Na)" should read -- ($Na_2SO_4$) --.

Column 14, line 18, "4(2,3-dihydroxyphenyl) butane" should read -- 4-(2,3-dihydroxyphenyl) butane --.

Column 14, line 35, "attracted" should read -- attached --.

Column 14, line 55, "Bis(1,4-" should be deleted.

Column 14, line 57, "Bis(1,4-" should be deleted.

Column 14, line 59, "Bis(1,4-" should be deleted.

Column 14, line 61, "Bis(1,4-" should be deleted.

Column 14, line 63, "Bis(1,4-" should be deleted.

Column 15, line 27, "3,4dihydroxyphenyl" should read -- 3,4-dihydroxyphenyl --.

Column 15, line 38, "dimethylbutene" should read -- dimethylbutadiene -- .

Column 15, line 43, "propane" should read -- propene --.

UNITED STATES PATENT AND TRADEMARK OFFICE
CERTIFICATE OF CORRECTION

PATENT NO. : 4,954,659

DATED : September 4, 1990

INVENTOR(S) : Robert M. Parkhurst et al.

It is certified that error appears in the above-identified patent and that said Letters Patent is hereby corrected as shown below:

Column 15, line 47, "dihyroxyphenyl" should read
-- dihydroxyphenyl --.

Column 15, line 67, "whenever" should read -- wherein --.

Column 16, line 32, "3,4dimethoxy" should read
-- 3,4-dimethoxy --.

UNITED STATES PATENT AND TRADEMARK OFFICE
CERTIFICATE OF CORRECTION

PATENT NO. : 4,954,659

DATED : September 4, 1990

INVENTOR(S) : Robert M. Parkhurst et al.

It is certified that error appears in the above-identified patent and that said Letters Patent is hereby corrected as shown below:

Column 16, line 33, "3,4methylenedioxy" should read
-- 3,4-methylenedioxy --.

Column 16, line 42, "benzyloxy5-" should read
-- benzyloxy-5- --.

Column 16, line 47, "3,-hydroxy-4,-carboxyphenyl" should read -- 3'-hydroxy-4'-carboxyphenyl --.

Signed and Sealed this

Twenty-eighth Day of July, 1992

*Attest:*

DOUGLAS B. COMER

*Attesting Officer*  *Acting Commissioner of Patents and Trademarks*